United States Patent [19]

Marks et al.

[11] Patent Number: 4,859,419
[45] Date of Patent: Aug. 22, 1989

[54] DIAGNOSTIC MANIFOLD APPARATUS

[75] Inventors: Martin E. Marks, Danville; William J. Littlehales, Point Richmond; Chu-An Chang, El Cerrito, all of Calif.

[73] Assignee: American Bionetics, Inc., Hayward, Calif.

[21] Appl. No.: 19,923

[22] Filed: Feb. 27, 1987

[51] Int. Cl.⁴ .................... G01N 21/78; G01N 33/52; G01N 33/547
[52] U.S. Cl. ........................................ 422/56; 422/69; 422/99; 422/102; 422/103; 422/104; 435/7; 435/312; 435/805
[58] Field of Search ............... 435/288, 312, 805, 809, 435/7; 422/56, 58, 59, 69, 99, 102, 103, 104

[56] References Cited
U.S. PATENT DOCUMENTS

| | | | |
|---|---|---|---|
| 3,582,284 | 6/1971 | Hamshere et al. | 422/103 |
| 4,031,197 | 6/1977 | Marinkovich et al. | 422/102 |
| 4,090,850 | 5/1978 | Chen et al. | 422/58 |
| 4,150,089 | 4/1979 | Linet | 422/103 |
| 4,332,768 | 6/1982 | Berglund | 422/103 |
| 4,558,013 | 12/1985 | Marinkovich et al. | 422/58 |
| 4,642,220 | 2/1987 | Björkman | 422/104 |
| 4,643,879 | 2/1987 | Hathaway | 422/102 |
| 4,649,028 | 3/1987 | Kaltenbach et al. | 422/103 |
| 4,725,406 | 2/1988 | Compton et al. | 422/58 |

Primary Examiner—Barry S. Richman
Assistant Examiner—Timothy M. McMahon
Attorney, Agent, or Firm—Fulwider, Patton, Reiber, Lee & Utecht

[57] ABSTRACT

Apparatus for immunoassay of multiple samples of biological fluids (e.g., AIDS antibodies), the apparatus being capable of mounting for rocking during incubation. A frame receives plural test vessels so that the vessels are interconnected for circulation through all the vessels of buffers, de-ionized water and air and for discharge of waste. Each vessel is transparent and contains nitrocellulose test paper impregnated with antigens to the antibodies. Valved ports in each vessel accept sequential insertion of the biological fluids, an enzyme conjugate and color developer. Color changes in the individual test papers are observed through the transparent vessels and identify presence of antibodies in the samples.

28 Claims, 3 Drawing Sheets

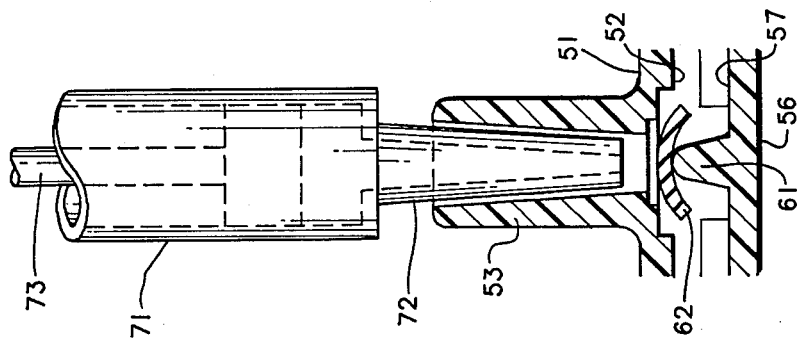
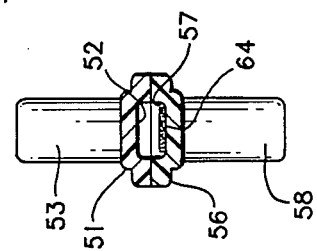
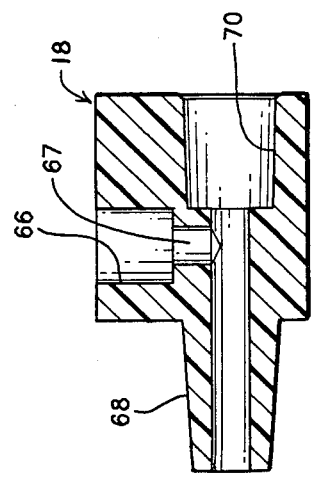
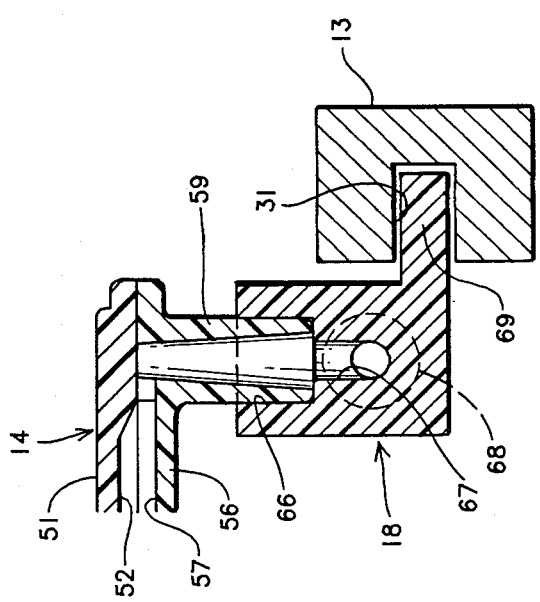
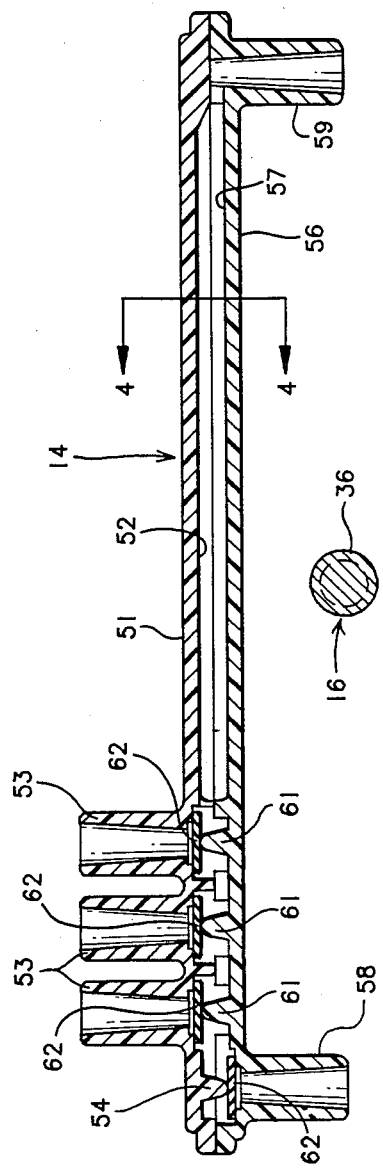

DIAGNOSTIC MANIFOLD APPARATUS

BACKGROUND OF THE INVENTION

1. Field of the Invention

This invention relates to a new and improved diagnostic manifold apparatus. A diagnostic procedure for analysis of certain antigens/antibodies in human blood sera, including particularly Acquired Immune Deficiency Syndrome (AIDS) is described by Tsang, V.C.W. et al. "Enzyme-Linked Immunoelectrotransfer Blot Technique (EIBT) (Western Blot) for HTLV-III/LAV Antibodies" (1985). Developmental Procedure. U.S. Department of Health and Human Services, Public Health Service, Center for Disease Control, Atlanta, Georgia, March 1985. Antigens derived from a virus are derived from the protein component of the virus and are a mixture of proteins, or oligopeptides, resulting from denaturing the protein component of the virus. The antigens which give rise to antibodies produced by the human host affected by the virus are included in the oligopeptides. Antigen mixtures are available from the National Cancer Institute, National Institutes of Health, Biological Modifier Program, Washington, D.C. as well as commercial sources.

The antigen mixture is separated into its components by electrophoresis onto a gel. The antigens in the gel are transferred to a paper strip such as nitrocellulose paper and are immobilized on the paper. To detect the presence of the virus in the human host, the paper is treated with human serum/plasma by an immunoassay method.

The present invention is useful in rapid, mass analysis such as would occur in a blood bank.

2. Description of Related Art

Equipment is available for similar assays as is described in European Patent Application 0119858 and International Patent Application WO 83/01308. Other devices for multiple assays are shown in U.S. Pat. Nos. 4,585,623; 3,884,641; 4,090,850. The present invention has numerous advantages over the aforementioned related art as hereinafter appears.

SUMMARY OF THE INVENTION

Narrow elongate strips of nitrocellulose or other suitable material impregnated with antigens to the antibodies to be tested are sealed in a rectangular cross-section transparent test vessel. This vessel has ports for the inlet and outlet of compressed air and various agents used during the tests. The inlets and outlets of adjacent identical test vessels interlock so that when the adjacent vessels are assembled in a frame they are interconnected for circulation of various agents from a manifold at one end of the frame through all of the vessels in the assembly and back to a discharge port in the manifold of the frame. Each vessel is also provided with readily accessible ports for the individual insertion of the serum to be tested, enzyme conjugates and color developer or other reagents. Preferably some or all of the ports are provided with check valves to permit only ingress of agents.

All of the test vessels are received in an open rectangular frame which may be mounted on a rocker to rock the contents of the vessels during incubation. At one end of the frame is the manifold heretofore described. Extending along either side are side members formed with longitudinal grooves into which tongues of connectors for the individual test vessels fit so that the vessels may slide longitudinally along the frame from an insert set position toward the manifold. A lead screw forces the test vessels toward the manifold and insures that the connections between adjacent vessels are fluid tight.

BRIEF DESCRIPTION OF THE DRAWINGS

The various aspects of the present invention will be discussed in more detail hereinafter in conjunction with the drawings wherein:

FIG. 2 is an enlarged fragmentary sectional view taken substantially along the line 2—2 of FIG. 1.

FIG. 3 is a sectional view taken substantially along the line 3—3 of FIG. 1.

FIG. 4 is a sectional view taken substantially along the line 4—4 of FIG. 3.

FIG. 5 is an enlarged sectional view taken substantially along the line 5—5 of FIG. 1.

FIG. 6 is an enlarged sectional view taken substantially along the line 6—6 of FIG. 1.

DESCRIPTION OF PREFERRED EMBODIMENT

Figure 1:
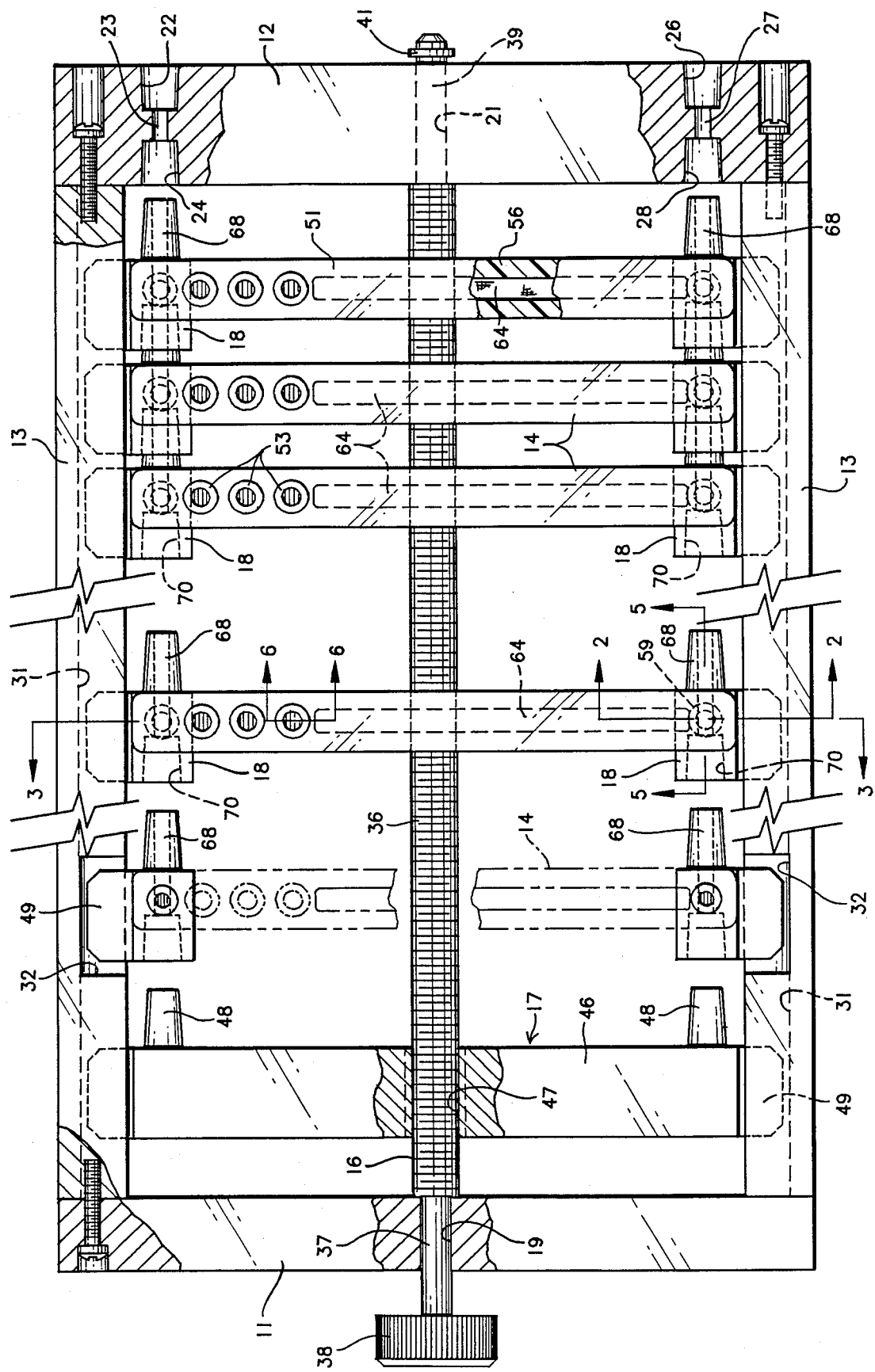
FIG. 1 is a top plan view of the device partially broken away in section to reveal internal construction.

An open rectangular frame is provided suitable for mounting in a conventional rocking mechanism of the general type commonly used during incubation of blood samples. The frame has a left end 11, a right end or manifold 12 and side rails 13 on either side. The ends and rails may be screwed together or otherwise connected. Removably received in the frame are a plurality of test vessels 14 which are inserted in the rails at the left end as viewed in FIG. 1 and forced towards the manifold end by a plug support 17 driven by a longitudinally extended, centrally disposed lead screw 16. Each test vessel 14 is provided at either end with a connector 18 which engages the rails 13 all as hereinafter explained. Lead screw 16 extends through a hole 19 in left frame end 11. The opposite end of screw 16 fits through hole 21 in manifold 12. Manifold 12 is formed with an inlet port 22 connected by duct 23 to an inlet receptor 24. Manifold 12 also has at its end opposite port 22 an outlet port 26 connected by duct 27 to outlet receptor 28. As hereinafter explained, fluids are applied to the inlet port 22, circulate through the test vessels 14 and are discharged back out of the outlet port 26 and into a waste receptacle.

Directing attention FIG. 2, each rail 13 is formed with a longitudinally extending rectangular cross-section groove 31. Spaced to the right of the left end of each rail 13 is formed an insert slot 32 into which tongues of sliding parts 17 and 18 fit.

Directing attention once again now to FIG. 1, the screw 16 has a threaded part 36 extending most of its length. At its left end it has a reduced diameter part 37 which fits through hole 19 in end 11 with a running fit and on its exterior it has a knob 38 which is used to turn the screw 16. At the right hand end of screw 16 is another reduced diameter portion 39 which fits into hole 21 in manifold 12 with a running fit. A conventional retainer 41 snaps into a groove (not shown) on the end of screw 16 to hold the parts assembled.

Plug support 17 has a rectangular cross-section transversely extending body 46 formed with a threaded hole 47 mating with the threaded portion 36 of screw 16. Plugs 48 in line with ports 22, 26 are formed extending to the right on one side of body 46. Projecting into slots 31 in side rails 13 are tongues 49 which fit into the slots 31 with a sliding fit. The insert slots 32 are located so that support 17 may be retracted to the left thereof making it possible for the tongues 49 to be inserted in insert slots 32.

Each test vessel 14 is formed of two molded parts formed of a transparent plastic material. The two parts are ultrasonically welded together after the paper strip 64 is installed on the bottom of the vessel. Thus, top 51 is formed with a longitudinally extending top groove 52. Extending upward from top 51 at the left end as viewed in FIG. 3 are three nipples 53. At the left end of top 51 is a downward projecting tip 54. Bottom 56 is formed with a bottom groove 57. At the left end of bottom 56 is a downward extending nipple 58 and at the right end is a similar downward projecting nipple 59. Nipple 58 is aligned with tip 54. Upward extending tips 61 on bottom 56 are aligned with nipples 53. Valve disks 62 are installed at the inner ends of each of the nipples 53 and 58 and bear against the tips 54 and 61. The disks 62 are preferably formed of a silicon rubber of 50 durometer and are approximately 0.010 inches thick. Hence the disks operate as check valves so that they permit ingress of fluid through the nipples 53 and 58.

As viewed in FIG. 4, the cross-section of the vessel 14 is rectangular and on the flat bottom thereof is a longitudinal extending test strip 64 of nitrocellulose paper or the like which has been suitably impregnated as heretofore described.

At each end of each test vessel 14 is a connector 18 best shown in FIGS. 2 and 5. Thus, at the top of connector 18 is an upward facing port 66 which receives either nipple 58 or 59 depending upon which end of the vessel 14 the connector 18 is installed. Projecting to the right as viewed in FIG. 1 on one side of each connector 18 is a nipple 68 which is connected by duct 67 to port 66. In alignment with nipple 68 is a receptor 70 which is positioned and shaped to receive either the nipple 68 of an adjacent test vessel 14 or one of the plugs 48 of plug support 17.

To assemble the device, the plug support 17 is retracted to the left as viewed in FIG. 1, clearing the insert slots 32. Test vessels 14 each having on its bottom a suitably impregnated paper 64 are attached at either end to a connector 18, the nipples 58 or 59 fitting into the port 66 of the connector. Each connector 18 has a tongue 69 shaped to be received in slot 31 of side rails 13 with a sliding fit. Thus, one after the other, the test vessels 14 are inserted in the frame through insert slots 32, the tongues 69 of the connectors being dropped into insert slots 32. As each vessel 14 is thus inserted in the slot 31, it is moved to the right. When the total number of vessels 14 to be tested have been thus inserted in the frame, they are moved to the right with the right most nipples 68 being received in the receptors 24, 28 and the corresponding nipple 68 of each vessel 14 being received in the receptor 70 of the next adjacent connector 18. Knob 38 is then turned, forcing plug support 17 towards the right as viewed in FIG. 1 until the plugs 48 enter the receptors 70 of the nearest vessel 14. Continued turning of the knob 38 forces all of the vessels 14 to the right, ensuring tight fits of the nipple 68 in the receptors 24 and 28 as well as in the receptor 70 of the adjacent connectors. With the completion of this operation, the apparatus is ready for the commencement of the assay process.

Figure 7:
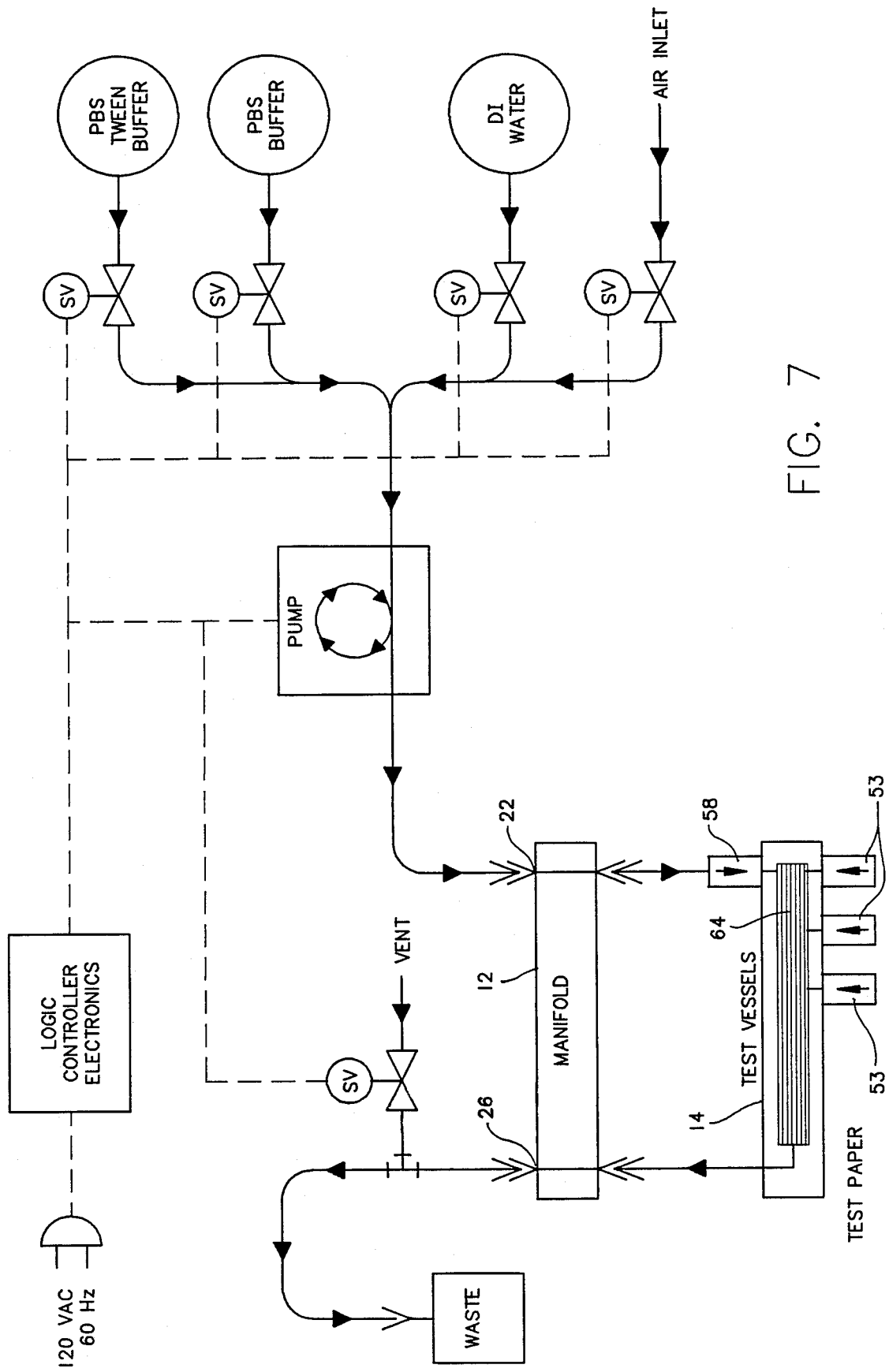
FIG. 7 is a schematic flow diagram.

Directing attention to FIG. 7, containers of solution designated in the drawing as PBS TWEEN buffer, PBS buffer and DI (de-ionized) water as well as a source of compressed air are connected through solenoid controlled valves SV to a pump which leads to the inlet port 22 of manifold 12. Because the connectors 18 of all of the vessels 14 are interconnected, whatever fluid is being pumped by the pump passes through all of the vessels 14. It will be understood that the pressure supplied by the pump causes the disks 62 to bend around the tips 54, permitting the fluid to flow into the left end (as viewed in FIG. 3) of each vessel 14 and then out the nipple 59 into the connector 18 and thence to the next connector 18 until the liquid passes back through the outlet port 26 of manifold 12 and thence to waste. The various solenoid valves of the pump are controlled by the logic controller electronics indicated in FIG. 7.

Thus more specifically, assuming that PBS buffer has been previously inserted in each vessel 14, the buffer is removed by opening the valve for the air inlet for approximately 30 seconds.

The next step in the procedure is to flush all of the vessels 14 with 25 ml of PBS TWEEN for 30 seconds. Air is then used to empty the PBS TWEEN buffer from each chamber by applying air for 30 seconds.

Directing attention now to FIG. 6, 1 ml of diluted serum is introduced into the test chamber through one of the nipples 53 from a syringe 71 which has a nipple 72 fitting into the nipple 53. Plunger 73 discharges the desired quantity of serum into the vessel, the pressure applied to the serum causing the valve disks 62 to bend as shown in FIG. 6 and permitting the serum to enter the test chamber. The serum is introduced through the check valve until the chamber is almost filled (the chamber should contain an air bubble about 5 mm long). The serum is then incubated in the chamber with the test strip for between 30 and 60 minutes at room temperature, the frame being rocked causing the bubble in the chamber to move up and down. The liquid is emptied from the chambers by opening the air inlet valve for about 30 seconds.

The next step is to rinse each chamber with 50 ml of PBS TWEEN buffer for about two minutes. Thereupon the liquid is emptied from the chambers using air for 30 seconds.

Enzyme conjugate (1 ml) is introduced into each chamber individually through the second of the nipples 53 until the chamber is almost filled but contains an air bubble about 5 ml long. Thereupon the frame is rocked allowing the conjugate to incubate for between 30 and 60 minutes at room temperature. The air inlet valve is opened emptying the liquid from the chambers for about 30 seconds.

Next, each chamber is rinsed with about 50 ml of PBS TWEEN buffer for about two minutes. The liquid is then emptied from the chamber using air for about 30 seconds. Another rinse of each chamber with about 50 ml of PBS buffer for about two minutes is performed and the liquid is emptied from the chambers with air for about 30 seconds.

Next, a 1 ml solution of diaminobenzedine with hydrogen peroxide (a color developer) is injected into each chamber individually through the third of the nipples 53. The color developer is allowed to incubate for 5 to 10 minutes at room temperature with rocking. Then the liquid is emptied from the chambers using air for about 30 seconds.

Finally, each chamber is rinsed with about 100 ml of de-ionized water for about four minutes.

Observation of the paper 64 in each chamber for band patterns identifies which particular antibodies are present in the serum which was injected into the system.

After the various vessels have been examined, the apparatus is disassembled and the frame is reused.

The individual test vessels 14 and connectors 18 may be discarded after use.

The volumes of fluids pumped through inlet 22 is sufficient so that said fluid opens valves 62 of all the test vessels 14 and completely fills all the vessels, any excess being discharged through nipple 59. Upon cessation of pumping, valves 62 close. Fluid in the test vessel chamber is trapped therein and does not run out since there would otherwise be a vacuum in the vessel. There is no cross-contamination because no back-flow differential occurs. Flushing the chamber causes a positive pressure in each vessel, again preventing cross-contamination.

Because the system is closed, there is no risk of contamination of operators or technicians, nor cross-contamination of samples.

It is believed that the invention is applicable not only in testing serum for AIDS but also for one or more of the following:

LYMES (arthritis)
HTLV-I (T-cell leukemia)
HTLV-II (multiple sclerosis).
HTLV-IV
LAV-II
Retroviruses
Autoimmune diseases

What is claimed is:

1. A test vessel for an assay apparatus comprising
an enclosed elongated body having an interior test chamber for receiving a test strip therein,
an inlet port at one end of the body in fluid communication with said chamber with means to connect the port to an inlet manifold,
an outlet port at the end of the body in fluid communication with said chamber opposite said inlet port with means to connect the outlet port to an outlet manifold,
at least one injection port disposed between the inlet port and the outlet port in fluid communication with said chamber, and
means to limit the flow of fluid into the interior test chamber through the inlet port and the injection port and out of the interior test chamber through the outlet port.

2. A test vessel according to claim 1 in which the means to control the flow comprises a check valve having flexible disk normally sealing off a port and means on the interior of said vessel bearing against the middle of said disk on the side of said disk opposite said port, whereby fluid pressure in said port bends said disk inward about said last-named means.

3. The vessel according to claim 1 having a plurality of injection ports spaced along the length of said test vessel and having separate check valves for each injection port.

4. The vessel according to claim 1 in which said inlet port includes a vertically-extending first nipple and the outlet port includes a vertically extending second nipple.

5. A test vessel according to claim 1 which includes a test paper impregnated with biological specimens along the bottom of said chamber.

6. The test vessel of claim 5 wherein the test paper is impregnated with biological specimens selected from the group consisting of antigens and antibodies.

7. The test vessel of claim 1 wherein the body is transparent.

8. The test vessel of claim 7 wherein the body has a rectangular transverse cross-section.

9. A multiple test chamber assay apparatus comprising
(a) a plurality of enclosed elongated test vessels, each test vessel having an interior test chamber therein adapted to receive a test strip, an inlet port at one end thereof, a discharge port at the other end thereof, at least one injection port disposed between the inlet port and outlet port which is in fluid communication with the test chamber and means to limit the flow of fluid into the interior test chamber through the inlet port and the injection port out of the interior test chamber through the outlet port;
(b) a common inlet manifold in fluid communication with inlet ports of the test vessels;
(c) a common outlet manifold in fluid communication with outlet ports of the test vessels;
(d) means to direct treatment fluids to the inlet manifold; and
(e) means to support the test vessels in a generally parallel relationship.

10. Apparatus according to claim 9 in which each of said test vessels are formed with at least one injection port spaced along the length of said test vessel having a check valve therein to allow fluid flow into the test chamber but prevent the discharge of fluid therefrom.

11. The assay apparatus of claim 9 wherein the fluid flow limiting means include check valves.

12. Apparatus according to claim 11 in which each of the check valves comprises a flexible disk normally sealing off said port and means on the interior of said vessel bearing against the middle of said disk on the side of said disk opposite said port, whereby fluid pressure in said port bends said disk inward about said last-named means.

13. The assay apparatus of claim 9 wherein the means to support the test vessels include a frame having parallel side rails.

14. The assay apparatus of claim 13 wherein the frame is adapted to pivot about an axis generally perpendicular to longitudinal axis of the test vessels.

15. The assay apparatus of claim 9 wherein the common inlet and outlet manifolds comprise an interfitting manifold segments.

16. The assay apparatus of claim 15 wherein the manifold segments include a male connection and a female connection, the male connection adapted to engage the female connection of an adjacent segment on one side of the test vessel and the female connection adapted to engage the male connection of an adjacent segment of a test vessel on the opposite side thereof.

17. The assay apparatus of claim 15 wherein each test vessel includes a pair of vertically extending nipples which depend from the test vessel, one of which cooperates with the inlet port to engage the inlet manifold segment in fluid communication and one which cooperates with the outlet port to engage the outlet manifold segment in fluid communication.

18. The assay apparatus of claim 17 wherein the inlet and outlet manifold segments are provided with vertical facing ports adapted to receive the depending nipples.

19. The assay apparatus of claim 15 wherein the manifold segments and provided with outwardly projecting tongues adapted to interfit recessed grooves provided within the side rails of the frame.

20. The assay apparatus of claim 19 including adjustable plug means slidably mounted on the side rails of the frame at one and thereof to seal open ends of the inlet and outlet manifold segments of a test vessel adjacent thereto.

21. The assay apparatus of claim 20 including fluid inlet and outlet conduits disposed on the end of the frame opposite the plug means adapted to engage the inlet and outlet manifold segments of a test vessel adjacent thereto.

22. The assay apparatus of claim 21 including means to urge the plug means and the inlet and outlet conduits together to fluidly interconnect with a plurality of test vessels therebetween.

23. The assay apparatus of claim 22 wherein the urging means includes an elongated threaded member interconnected with the means and means to rotate the threaded means to move the plug means longitudinally along the frame.

24. A multiple test vessel assay system comprising:
    (a) a plurality of test vessels, each test vessel having at least an inlet port and an outlet port in fluid communication with an interior test chamber therein adapted to receive a test strip;
    (b) means to limit the flow of fluid into the interior test chamber through the inlet port and out of the interior test chamber through the outlet port;
    (c) a common inlet manifold in fluid communication with the inlet ports of said test vessels;
    (d) a common outlet manifold in fluid communication with the outlet ports of said test vessels;
    (e) a plurality of conduits with each of the conduits in fluid communication with a separate fluid source and the common inlet manifold; and
    (f) automatically controlled valve means in said conduits to control the sequenceing of fluid flow from said sources into the common inlet manifold through said conduits.

25. The assay system of claim 24 wherein the test vessels have injection ports in fluid communication with the interior test chamber with means to restrict flow therethrough into the interior test chamber.

26. The assay system of claim 24 including a frame for holding the test vessels in a generally parallel relationship.

27. The assay system of claim 24 including an electronic controller to automatically sequence the opening and closing of said valve means to provide a desired sequence of treatment fluids to each of said test vessels.

28. The assay system of claim 24 wherein the inlet and outlet manifolds comprise a plurality of individual interfitting manifold segments.

* * * * *